(12) United States Patent
Schelberger et al.

(10) Patent No.: US 6,365,614 B1
(45) Date of Patent: Apr. 2, 2002

(54) FUNGICIDES MIXTURES

(75) Inventors: Klaus Schelberger, Gönnheim; Maria Scherer, Landau; Hubert Sauter, Mannheim; Bernd Müller, Frankenthal; Erich Birner, Altleiningen; Joachim Leyendecker, Ladenburg; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/445,185

(22) PCT Filed: Jun. 5, 1998

(86) PCT No.: PCT/EP98/03367

§ 371 Date: Dec. 8, 1999

§ 102(e) Date: Dec. 8, 1999

(87) PCT Pub. No.: WO98/58544

PCT Pub. Date: Dec. 30, 1998

(30) Foreign Application Priority Data

Jun. 19, 1997 (DE) .......................................... 197 25 947

(51) Int. Cl.⁷ .................... A01N 43/64; A01N 43/56; A01N 43/08; A01N 43/76; A01N 37/18

(52) U.S. Cl. .................... 514/384; 514/374; 514/407; 514/471; 514/538; 514/539; 514/619; 514/472

(58) Field of Search .................... 514/407, 384, 514/538, 539, 619, 472, 471, 374

(56) References Cited

U.S. PATENT DOCUMENTS

| | | | | |
|---|---|---|---|---|
| 4,829,085 A | 5/1989 | Wenderoth et al. | .......... | 514/522 |
| 5,185,342 A | 2/1993 | Hayase et al. | .............. | 514/274 |
| 5,395,854 A | 3/1995 | Brand et al. | ................. | 514/619 |

FOREIGN PATENT DOCUMENTS

| | | |
|---|---|---|
| EP | 0253 213 | 1/1988 |
| EP | 0398 692 | 11/1990 |
| EP | 0477 631 | 4/1992 |
| EP | 0741 970 | 11/1996 |
| WO | 96/01256 | 1/1996 |
| WO | 96/01258 | 1/1996 |
| WO | 96/03047 | 2/1996 |
| WO | 97/00011 | 1/1997 |

OTHER PUBLICATIONS

Azoxystrobin Compositions, Res. Disc. Nr. 390, Oct. 10, 1996 672–674.

Primary Examiner—Allen J. Robinson
(74) Attorney, Agent, or Firm—Keil & Weinkauf

(57) ABSTRACT

A fungicidal mixture, comprising at least one active compound selected from $a_1$) carbamates of the formula Ia,

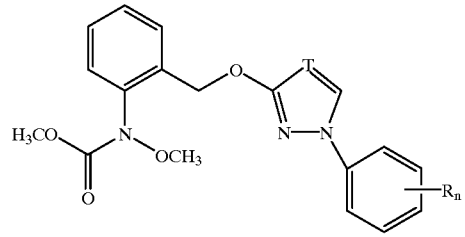

(Ia)

where T is CH or N, n is 0, 1 or 2 and R is halogen, $C_1$–$C_4$-alkyl or $C_1$–$C_4$-haloalkyl, it being possible for the radicals R to be different if n is 2, and $a_2$) the oxime ether carboxylic ester of the formula Ib

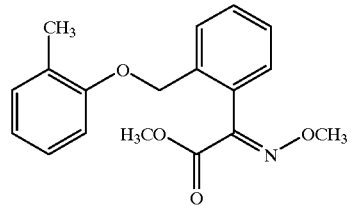

(Ib)

$a_3$) the oxime ether carboxamide of the formula Ic

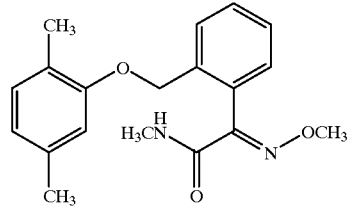

(Ic)

b) at least one active compound of the formulae II.1. to II.5.

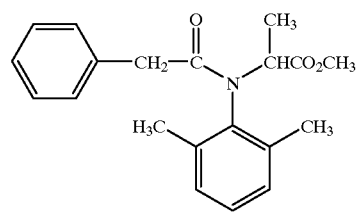

(II.1)

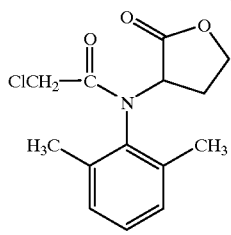

(II.2)

-continued
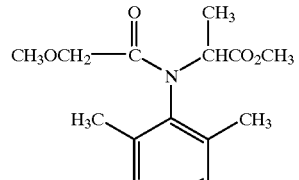
(II.3)
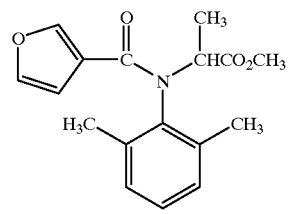
(II.4)
-continued
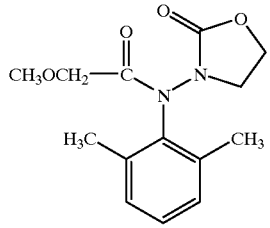
(II.5)
in a synergistically effective amount, and methods for their use as fungicides, are described.
18 Claims, No Drawings

FUNGICIDES MIXTURES

This application is a 371 of PCT/EP98/03367, filed Jun. 5, 1998.

The present invention relates to fungicidal mixtures which comprise at least one active compound selected from $a_1$) carbamates of the formula Ia,

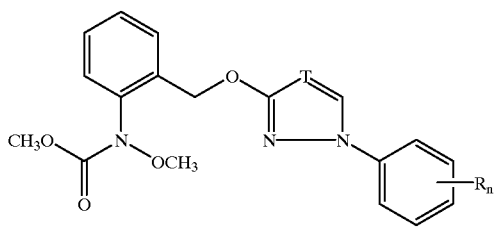
(Ia)

where T is CH or N, n is 0, 1 or 2 and R is halogen, $C_1$–$C_4$-alkyl or $C_1$–$C_4$-haloalkyl, it being possible for the radicals R to be different if n is 2, $a_2$) the oxime ether carboxylic ester of the formula Ib

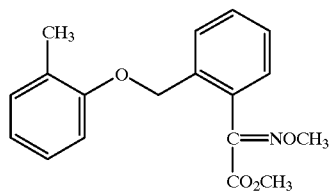
(Ib)

$a_3$) the oxime ether carboxamide of the formula Ic

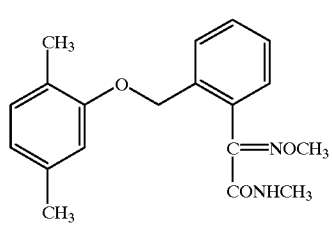
(Ic)

and b) at least one active compound of the formulae II.1 to II.5,

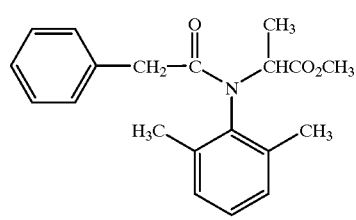
(II.1)

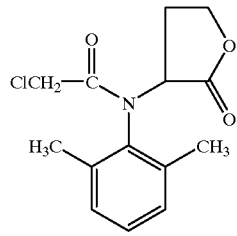
(II.2.)

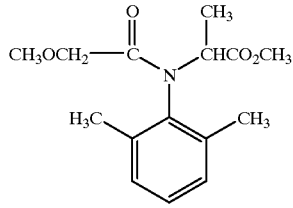
(II.3)

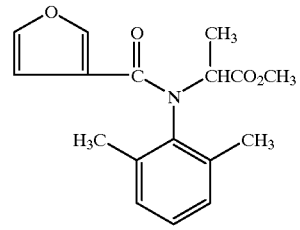
(II.4)

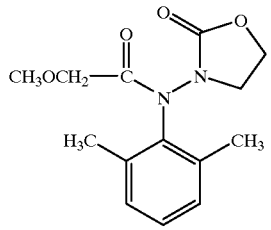
(II.5)

in a synergistically effective amount.

Moreover, the invention relates to methods for controlling harmful fungi using mixtures of the compounds I and II and to the use of the compounds I and II for preparing such mixtures.

The compounds of the formula Ia, their preparation and their activity against harmful fungi are disclosed in the literature (WO-A 96/01,256 and 96/01,258).

The compounds of the formulae Ib and Ic, their preparation and their activity against harmful fungi are disclosed in the literature (EP-A 253 213, EP-A 398 692 and EP-A 477 631).

The compound II.1. is commercially available under the common name benalaxyl or the trade name Galben™.

The compound II.2. is commercially available under the common name Ofurace or the trade name Celtan™ P in the form of mixtures with cymoxanil and folpet.

The compound II.3. is commercially available under the common name metalaxyl or the trade name Ridomil™.

The compound II.4. is commercially available under the common name furalaxyl or the trade name Fongaride™.

The compound of the formula II.5. is known under the common name oxadixyl and commercially available under the trade name Sandofan™ C. in mixtures with copper salts.

Processes for preparing the compounds of the formula II are known per se to the person skilled in the art and therefore require no further explanation.

It is an object of the present invention to provide mixtures which have an improved activity against harmful fungi combined with a reduced total amount of active compounds applied (synergistic mixtures), with a view to reducing the application rates and improving the activity spectrum of the known compounds.

We have found that this object is achieved by the mixtures defined at the outset. Moreover, we have found that applying the compounds I and II simultaneously, ie. together or separately, or applying the compounds I and II in succession provides better control of harmful fungi than is possible with the individual compounds alone.

The formula Ia represents, in particular, carbamates in which the combination of substituents corresponds to one line of the table below:

TABLE 1

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Particular preference is given to the compounds I.12, I.23, I.32 and I.38.

The present invention includes both binary mixtures of active compounds of the formula I with one of the compounds II.1. to II.5. and mixtures comprising a plurality of active compounds of the formula I and/or a plurality of active compounds of the formula II.

In some instances, mixtures of one or more active compounds of the formula Ia and one or more active compounds of the formulae II.1. to II.5. have proven to be particularly advantageous.

In relation to the C=Y or C=CH or C=N double bonds, the compounds of the formulae Ia and Ib can be present in the E or the Z configuration (in relation to the carboxylic acid function). Accordingly, they can be used in the mixture according to the invention in each case either as pure E or Z isomers or as E/Z isomer mixtures. The E/Z isomer mixture or the Z isomer is preferably used, the Z isomer being particularly preferred.

The C=N double bonds of the oxime ether groups in the side chain of the compounds Ia can exist in each case as pure E or Z isomers or as E/Z isomer mixtures. The compounds Ia can be used in the mixtures according to the invention both as isomer mixtures and as pure isomers. With a view to their use, compounds Ia which are particularly preferred are those where the terminal oxime ether grouping in the side chain is in the cis configuration ($OCH_3$ to ZR').

Owing to their basic character, the compounds Ia, Ib and Ic are capable of forming salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carboxylic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals with 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphoric acid radicals), it being possible for the alkyl or aryl radicals to carry further substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth subgroup, in particular chromium, manganese, iron, cobalt, nickel, copper and zinc, and others. Particular preference is given to the metal ions of the elements of the subgroups of the fourth period. The metals can exist in the various valencies which they can assume.

When preparing the mixtures, it is preferred to employ the pure active compounds Ia, Ib and/or Ic and II.1 to II.5., with which further active compounds against harmful fungi or other pests, such as insects, arachnids or nematodes, or else herbicidal or growth-regulating active compounds or fertilizers can be admixed as required.

As α-amino derivatives, the compounds of the formulae II.1. to II.4. have an asymmetric carbon atom and can therefore be present and employed both as racemates and as optically pure isomers. Thus, the optically pure R enantiomer of the compound II.3., for example, is known under the common name metalaxyl-M (C. Nuninger, G. Watson, N. Leadbitter and H. Ellgehausen, Proc. of Brighton Crop Protection Conf. 1996, Vol. 1, p. 41–46) und commercially available under the trade name Ridomil™ or Apron™ XL.

The mixtures of the compounds I and II, or the simultaneous, joint or separate use of the compounds I and II, have outstanding action against a wide range of phytopathogenic fungi, in particular from the classes of the Ascomycetes, Deuteromycetes, Phycomycetes and Basidiomycetes. Some of them act systemically and are therefore also suitable for use as foliar and soil-acting fungicides.

They are especially important for controlling a large number of fungi in a variety of crop plants, such as cotton, vegetable species (for example cucumbers, beans and cucurbits), barley, grass, oats, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalies* (scab) in applies, Helminthosporium species in cereals, *Septoria nodorum* in wheat, *botrytis cinerea* (gray mold) in strawberries, vegetables, ornametals and grapevines, *Cercospora arachidicola* in groundnuts, *Pseudocercosporella heroptrichoides* in wheat and barley, *Pyricularia oryzae* in rice, *Phytophthora infestans* in potatoes and tomatoes, Pseudoperonospora species in cucurbits and hops, *Plasmopara viticola* in grapevines, Alternaria species in vegetables and fruit and Fusarium and Verticillim species.

Furthermore, they can be used in the protection of materials (eg. in the protection of wood), for example against *Paecilomyces variotii*.

The compounds I and II can be applied simultaneously, either together or separately, or in succession, the sequence, in the case of separate application, generally not having any effect on the control results.

The compounds I and II are usually applied in a weight ratio of from 0.05:1 to 20:1, preferably from 0.1:1 to 10:1, in particular from 0.2:1 to 5:1 (II:I).

Depending on the nature of the desired effect, the application rates of the mixtures according to the invention are, for the compounds I, from 0.005 to 0.5 kg/ha, preferably from 0.05 to 0.5 kg/ha, in particular from 0.05 to 0.2 kg/ha.

Correspondingly, the application rates of the compounds II are usually from 0.005 to 1 kg/ha, preferably 0.05 to 1 kg/ha, in particular 0.05 to 0.5 kg/ha.

For seed treatment, the application rates of the mixture are generally from 0.001 to 100 g/kg of seed, preferably 0.01 to 50 g/kg, in particular 0.01 to 10 g/kg.

If phytopathogenic harmful fungi are to be controlled, the separate or joint application of the compounds I and II or of the mixtures of the compounds I and II is effected by spraying or dusting the seeds, the plants or the soils before or after sowing, or before or after plant emergence.

The fungicidal synergistic mixtures according to the invention, or the compounds I and II, can be formulated for example in the form of ready-to-spray solutions, powders and suspensions or in the form of highly concentrated aqueous oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform a distribution as possible of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl, octyl or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene or polyoxpropylene alkyl ethers, lauryl alcohol polyglycol ether acetate, sorbitol esters, lignosulfite waste liquors or methylcellulose.

Granules (eg. coated granules, impregnated granules or homogeneous granules) are usually prepared by binding the active compound, or active compounds, to a solid carrier.

Fillers or solid carriers are, for example, mineral earths, such as silica gel, silicic acids, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I or II or of the mixture of the compounds I and II. The active compounds are employed in a purity of from 90% to 100%, preferably from 95% to 100% (according to NMR or HPLC).

The compounds I or II, the mixtures or the corresponding formulations are applied by treating the harmful fungi, the plants, seeds, soils, areas, materials or spaces to be kept free from them with a fungicidally effective amount of the mixture, or of the compounds I and II in the case of separate applications. Application can be effected before or after infection by the harmful fungi.

The fungicidal activity of the compound and of the mixtures can be demonstrated by the following experiments:

Curative action against Plasmopara viticola

Leaves of potted grapevines cv. "Müller-Thurgau" were inoculated with an aqueous zoospore suspension of Plasmopara viticola. The grapevines were subsequently kept in a water-vapor-saturated chamber at 22–24° C. for 48 hours. They were then removed from the chambers and, after they had dried, sprayed to run off point with an aqueous preparation of active compound which had been prepared from a stock solution comprising 10% of active compound, 63% of cyclohexanone and 27% of emulsifier. After the spray coating had dried on, the plants were cultivated for another 5 days in the greenhouse at 20–30° C. After this time, the plants were returned into a humid chamber for 16 hours to accelerate the eruption of sporangiophore. The extent to which the disease had developed on the undersides of the leaves was then determined visually in %.

Evaluation is carried out by determining the infected leaf areas in percent. These percentages are converted into efficacies. The expected efficacies of the active compound mixtures are determined using Colby's formula [R. S. Colby, Weeds 15, 20–22 (1967)] and compared with the observed efficacies. Colby's formula:

$$E = x + y + z - x \cdot y \cdot z / 100$$

expected efficacy, expressed in % of the untreated control, when using the mixture of the active compounds A, B and C at the concentrations a, b and c
   x efficacy, expressed in % of the untreated control, when using active compound A at a concentration of a
   y efficacy, expressed in % of the untreated control, when using active compound B at a concentration of b
   z efficacy, expressed in % of the untreated control, when using active compound C at a concentration of c The efficacy(E) is calculated as follows using Abbot's formula:

$$E = (1 - \alpha) \cdot 100 / \beta$$

α corresponds to the fungal infection of the treated plants in % and
β corresponds to the fungal infection of the untreated (control) plants in %

An efficacy of 0 means that the infection level of the treated plants corresponds to that of the untreated control plants; an efficacy of 100 means that the treated plants were not infected.

The test results are shown in Tables 2 and 3 below.

TABLE 2

| Ex. | Active compound | Concentration of active compound in the spray liquor in ppm | Efficacy in % of the untreated control |
|---|---|---|---|
| 1C | Control (untreated) | (73% infection) | 0 |
| 2C | Compound I.32 of Tab. 1 (Ia.1) | 16<br>4<br>1 | 45<br>0<br>0 |
| 3C | Compound I.38 of Tab. 1 (Ia.2) | 1 | 0 |
| 4C | II.2 (Ofurace) | 16<br>4<br>1 | 73<br>73<br>0 |
| 5C | II.3 (Metalaxyl) | 1 | 59 |

TABLE 3

| Ex. | According to the invention | Observed efficacy | Calculated efficacy[*)] |
|---|---|---|---|
| 6 | 16 ppm Ia.1 + 16 ppm II.2 | 96 | 85 |
| 7 | 4 ppm Ia.1 + 4 ppm II.2 | 96 | 73 |
| 8 | 1 ppm Ia.1 + 1 ppm II.2 | 30 | 0 |
| 9 | 1 ppm Ia.1 + 1 ppm II.3 | 90 | 59 |
| 10 | 1 ppm Ia.2 + 1 ppm II.2 | 40 | 0 |

[*)]Calculated using Colby's formula

The test results show that the observed efficacy in all mixing ratios is higher than the efficacy which had been calculated beforehand using Colby's formula.

What is claimed is:
1. A fungicidal composition comprising synergistically effective amounts of a) a first active component (I) which is at least one active compound selected from the group of carbamates of formula Ia,

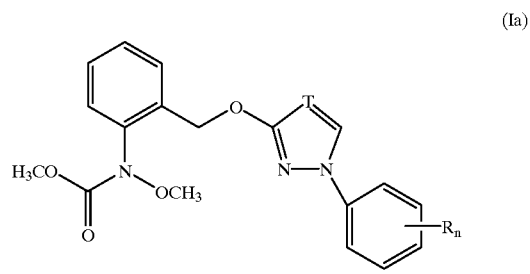

(Ia)

wherein T is CH or N, n is 0, 1 or 2 and R is halogen, $C_1$–$C_4$-alkyl or $C_1$–$C_4$-haloalkyl, where the radicals R are identical or different when n is 2, and b) a second active component (II) which is at least one of the compounds of formulae II.1 to II.5

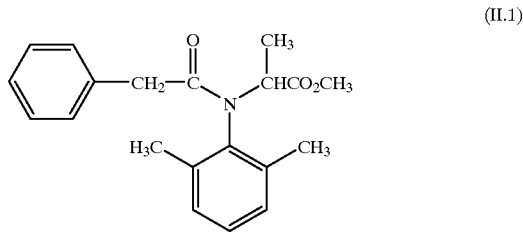

(II.1)

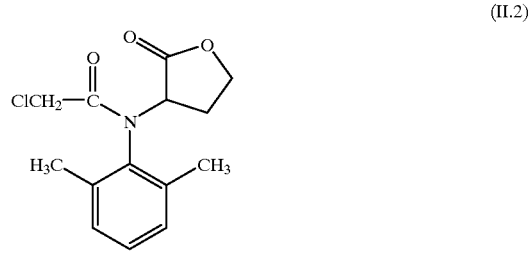

(II.2)

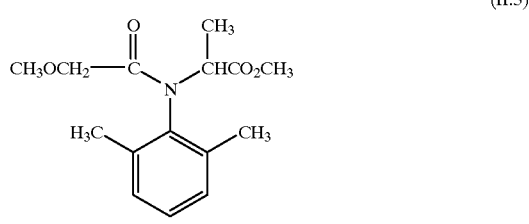

(II.3)

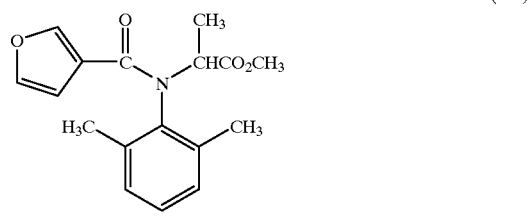

(II.4)

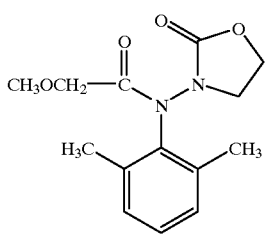
(II.5)

2. The composition defined in claim 1, wherein the active component (II) comprises the compound of formula II.1.

3. The composition defined in claim 1, wherein the active component (II) comprises the compound of formula II.2.

4. The composition defined in claim 1, wherein the active component (II) comprises the compound of formula II.3.

5. The composition defined in claim 1, wherein the active component (II) comprises the compound of formula II.4.

6. The composition defined in claim 1, wherein the active component (II) comprises the compound of formula II.5.

7. The composition defined in claim 1, wherein the active component (I) additionally comprises an oxime ether compound of formula I.b or I.c

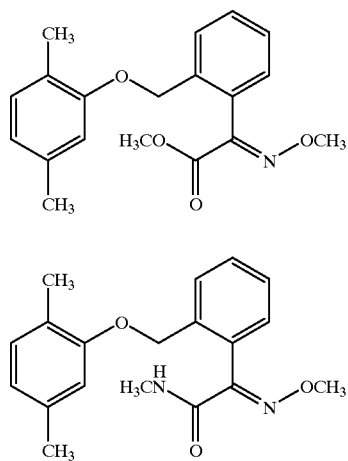

or both the oxime ether compounds of formula I.b and I.c.

8. The composition defined in claim 7, wherein the active component (II) comprises the compound of formula II.1.

9. The composition defined in claim 7, wherein the active component (II) comprises the compound of formula II.2.

10. The composition defined in claim 7, wherein the active component (II) comprises the compound of formula II.3.

11. The composition defined in claim 7, wherein the active component (II) comprises the compound of formula II.4.

12. The composition defined in claim 7, wherein the active component (II) comprises the compound of formula II.5.

13. A method for controlling harmful fungi, which comprises treating the fungi, their habitat or plants, seeds, soils, areas, materials or spaces to be kept free from said fungi with synergistically effective amounts of component (I) and component (II), wherein components (I) and (II) are as defined in claim 1.

14. The method of claim 13, wherein the the active component (I) is applied in an amount of from 0.005 to 0.5 kg/ha.

15. The method of claim 13, wherein the the active component (II) is applied in an amount of from 0.005 to 1 kg/ha.

16. The method of claim 13, wherein the the active component (I) additionally comprises an oxime ether compound of formula I.b or I.c

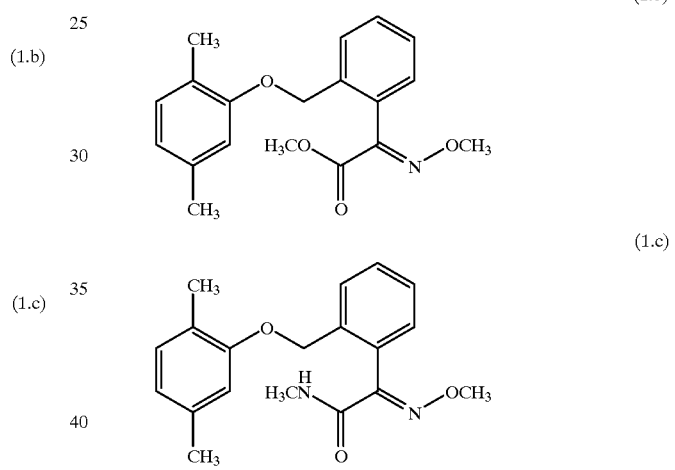

or both the oxime ether compounds of formula I.b and I.c.

17. The method of claim 16, wherein the the active component (I) is applied in an amount of from 0.005 to 0.5 kg/ha.

18. The method of claim 16, wherein the the active component (II) is applied in an amount of from 0.005 to 1 kg/ha.

* * * * *